United States Patent
Cossee et al.

(10) Patent No.: US 6,488,856 B2
(45) Date of Patent: Dec. 3, 2002

(54) PROCESS FOR PURIFYING A LIQUID HYDROCARBON PRODUCT

(75) Inventors: Robert Paul Cossee, Amsterdam (NL); Eduard Rudolf Geus, Amsterdam (NL); Edward Jan Van Den Heuvel, Rotterdam (NL); Cornelis Everardus Weber, Rotterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/785,125

(22) Filed: Oct. 9, 2001

(65) Prior Publication Data

US 2002/0017490 A1 Feb. 14, 2002

(30) Foreign Application Priority Data

Feb. 17, 2000 (EP) .............................. 00200548

(51) Int. Cl.[7] .......................... B01D 61/00; B01D 61/36
(52) U.S. Cl. ................... 210/644; 210/652; 210/654; 585/648
(58) Field of Search ................... 210/640, 652, 210/500.27, 500.35, 654, 490, 644; 585/648

(56) References Cited

U.S. PATENT DOCUMENTS

| 5,151,182 A | * | 9/1992 | Perry et al. |
| 5,205,934 A | * | 4/1993 | Linder et al. |
| 5,265,734 A | * | 11/1993 | Linder et al. |
| 5,965,015 A | * | 10/1999 | Ronan et al. |
| 6,013,852 A | * | 1/2000 | Chandrasekharan et al. |

* cited by examiner

Primary Examiner—Ana Fortuna

(57) ABSTRACT

The invention relates to a process for purifying a liquid hydrocarbon product consisting of 5% by weight or less of high molecular weight contaminants having a molecular weight of at least 1000, wherein the product stream is contacted with a hydrophobic non-porous or nano-filtration membrane and the purified product stream is recovered as the permeate. Various liquid hydrocarbon products can be treated including process streams containing as the main product styrene, isoprene, butadiene, pentadiene, dicyclopentadiene, piperylene, $C_2$–$C_5$ mono-olefins or acrylates.

2 Claims, 1 Drawing Sheet

PROCESS FOR PURIFYING A LIQUID HYDROCARBON PRODUCT

FIELD OF THE INVENTION

The present invention relates to a process for purifying a liquid hydrocarbon product by removing high molecular weight contaminants.

BACKGROUND OF THE INVENTION

Many liquid hydrocarbon products are available, which contain high molecular weight contaminants. The contamination normally originates in the process producing the product and is due to undesirable polymerisation of substances intrinsically present in the process. Such polymerisable substances may be the liquid hydrocarbon product itself (e.g. styrene, butadiene, isoprene), but can also be one or more other monomers intrinsic to the process for producing the hydrocarbon product. Such other monomer may itself be a separate product of the process. The polymerisable substances have in common that they are prone to polymerisation under the process conditions. For instance, dicyclopentadiene and cis- and trans-1,3-pentadiene (piperylene) may contain small amounts of polyisoprene, because both are typically produced from the $C_5$-cut of a cracked effluent stream from which isoprene is produced. Thus, isoprene is intrinsically present in the process producing piperylene or dicyclopentadiene and may form polyisoprene.

Furthermore, if a polymerisable hydrocarbon product (e.g. styrene) is used as a feedstock for the production of a homopolymer, copolymer or block copolymer (e.g. syndiotactic polystyrene, random styrene-butadiene copolymer or styrene-butadiene block copolymer), the product itself may be forming an uncontrolled polymeric contaminant under the right conditions. Apart from the fact that such polymeric contaminant may interfere in an undesirable manner with the formation of the envisaged polymer, it will also normally have a reactivity which is different from the envisaged polymer. This latter aspect could cause difficulties when processing the envisaged polymer into the endproduct.

The undesirable polymerisation may occur due to reactions caused by the presence of traces of substances forming polymerisation initiators which are difficult to remove or avoid. Such initiators could be radicals formed from peroxides, which in turn can be formed from oxygen ingress in the presence of olefins or other compounds having an unsaturated double bond (C=C). Polymerisation may also occur due to the presence of substances which act as catalyst for the polymerisation reaction, especially where this catalyst is a substance intrinsic to the process.

The high molecular weight contaminants are typically present in relatively small amounts up to 5% by weight based on total weight of the liquid product. However, often amounts as low as 3% by weight or less or even 1% by weight or less already make the product less suitable or even completely unsuitable for subsequent processing or for direct end use.

In order to benefit from the process of the present invention, the liquid hydrocarbon products to be subjected to the process of the present invention will usually contain at least 0.00001% wt of high molecular weight contaminants, more specifically at least 0.001% wt. However, in some cases even smaller amounts can make use of the process of the present invention attractive.

In general, several separation techniques are known in the art for separating contaminants from the actual product based on the difference in molecular weight. One such known and applied technology is distillation, wherein a separation takes place on the basis of differences in boiling points between the various components, which differences are related to the differences in volatility between the various components. However, the fact that high molecular weight contaminants are present in such small amounts makes distillation a relatively expensive way of purifying the product. Namely, in distillation the actual product forming the bulk of the stream to be treated would have to be evaporated, recovered as the gaseous top fraction and subsequently condensed for further use, whereas the high molecular weight contaminants would have to be recovered as the liquid bottom fraction. Beside the energy-intensive nature of this treatment, a lot of equipment would also be required to carry out the distillation. Moreover, the high temperatures normally applied in distillation increase the likelihood of (thermal) decomposition of the hydrocarbon product. This could lead to product loss and fouling of the equipment. The application of high temperatures could be avoided by performing the distillation at low pressure, but this would increase the risk on oxygen ingress, which in return could lead to the formation of peroxides. As explained above, these peroxides will induce polymerization reactions. Furthermore, low pressure distillation would necessitate the use of more expensive equipment. It will be appreciated that these factors render the distillation unattractive from an economic perspective.

The present invention aims to provide a method for effectively and cost-efficiently removing the high molecular weight contaminants.

SUMMARY OF THE INVENTION

Accordingly, the present invention relates to a process for purifying a liquid hydrocarbon product comprising 5% by weight or less of high molecular weight contaminants having a molecular weight of at least 1000, said process comprising contacting the product stream with a hydrophobic non-porous or nano-filtration membrane to produce a purified product stream and recovering the purified product stream as permeate.

BRIEF DESCRIPTION OF THE DRAWING

The FIGURE shows GPC results of the retentate and permeate after use of the invention.

DETAILED DESCRIPTION OF THE INVENTION

Figure 1:
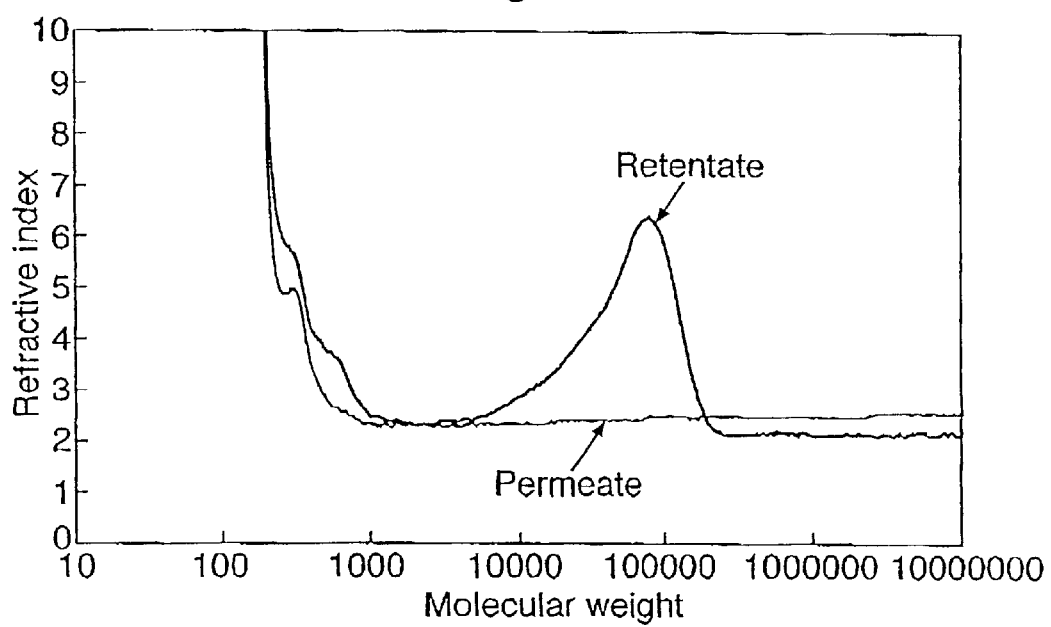

The molecular weights as used throughout this specification are expressed in Dalton and are based on a determination by gel permeation chromatography (GPC) using polystyrene calibration standards.

The present invention provides a method of removing high molecular weight contaminants from the liquid hydrocarbon product by using a membrane separation treatment.

The advantage of using a membrane separation is that, as opposed to distillation, there is no need to change the phase of the hydrocarbon to be treated. This saves on energy and equipment costs. As opposed to absorption, the membrane separation does not require a desorption step nor does it result in a voluminous reject consisting of the laden sorbent, which is also a possible consequence of absorption. As opposed to membrane separation over a porous membrane, the presently proposed membrane separation has the advantage that no blocking of membrane pores can occur, as the transmission of the permeate takes place via the solution-diffusion mechanism (see hereinafter).

The separation in accordance with the process of the present invention aims to split the product into two fractions: a permeate and a retentate. The permeate has been upgraded in the sense that its contamination level has been lowered. Consequently the permeate has obtained a higher value compared to the original product. The retentate, which contains an increased proportion of contaminants as compared to the original product, has a value depending on the concentration of the contamination (resultant of the separation) and the perceived end use. The retentate value may be lower than or similar to the value of the original feed. The stage cut-defined as the weight percentage of the original product stream that passes through the membrane and is recovered as permeate- can vary within broad limits: 10 to 99% by weight, preferably 30 to 95% by weight. In case the retentate still has a value close to that of the original product, the stage cut will be relatively low, whereas if the value of the retentate can be much lower than the value of the original product the objective will be to recover as much permeate as possible. Thus, a further advantage of the present invention is that besides the permeate, which always has a higher value than the original product, the retentate can also have a relatively high value by proper control of the stage cut.

The liquid hydrocarbon product to be treated contains 5% by weight or less of high molecular weight contaminants based on total weight of the liquid product. However, the present method is particularly suitable when the liquid hydrocarbon product to be treated contains 3% by weight or less, more suitably 1% by weight or less of high molecular weight contaminants. Even at high molecular weight contaminant levels of 0.1% by weight or less the method of the present invention is highly effective.

The liquid hydrocarbon product to be treated may be an industrially produced chemical product stream comprising the desired chemical product and 5% by weight or less of high molecular weight contaminants, wherein the desired chemical product is a hydrocarbon optionally comprising one or more hetero-atoms and suitably has a molecular weight of less than about 250, more suitably less than about 200 and even more suitably less than about 150. The molecule of the desired chemical product suitably comprises at least one moiety through which polymerization (including copolymerisation) can occur, which moiety preferably is a polymerisable olefinic bond.

Accordingly, one class of suitable chemical products, which can be purified by the process of the present invention, are mono-olefins of the general formula (I)

$$R_1R_2C=CR_3R_4 \quad (I)$$

wherein $R_1$, $R_2$, $R_3$ and $R_4$ may be the same or different and independently represent hydrogen, $C_1-C_5$ alkyl, $C_1-C_5$ alkenyl, aryl (preferably phenyl), CN, Cl or a group C(O) $OR_5$ with $R_5$ representing a $C_1-C_4$ alkyl group. It is preferred that $R_1$ represents a group as indicated, while $R_2$, $R_3$ and $R_4$ represent hydrogen.

Another class of suitable olefinically unsaturated compounds are the conjugated dienes, which can be characterised by the general formula (II)

$$R_1R_2C=CHR_6-CHR_7=CR_3R_4 \quad (II)$$

wherein $R_1$, $R_2$, $R_3$ and $R_4$ have the same meaning as in formula (I) and $R_6$ and $R_7$ may be the same or different and independently represent hydrogen or $C_1-C_4$ alkyl, preferably methyl or ethyl.

Yet another class of suitable chemical products are the compounds containing one or more olefinic bonds in a cyclic structure. Useful compounds of this type are alicyclic mono- and diolefins, such as cyclopentadiene, dicyclopentadiene, 1,3-cyclohexadiene and cyclohexene.

Preferred chemical products comprise up to 15 carbon atoms, more suitably from 4 to 10 carbon atoms, and examples include styrene, isoprene, butadiene, cis-1,3-pentadiene, trans-1,3-pentadiene, benzene, toluene, xylenes, $C_2-C_5$ mono-olefins (suitably, ethene and propene) and acrylates, like methyl acrylate, ethyl acrylate and methylmethacrylate.

Of all products mentioned, dicyclopentadiene and styrene are preferred for the purpose of the present invention.

The high molecular weight contaminants have a molecular weight of at least 1000. In the process of the present invention at least 80% by weight of all contaminants having a molecular weight of at least 1000 are removed, suitably at least 90% by weight and more suitably at least 95% by weight is removed. Most suitably, 99% by weight or more of these contaminants is removed. It is preferred that the contaminants which have a molecular weight of at least 2500 are effectively removed, while contaminants having a molecular weight of at least 5000 are even more preferably effectively removed to ensure optimum endproduct quality. Effective removal in this context means that at least 95% by weight and more suitably at least 99% by weight of said contaminants is removed. The upper limit for the molecular weight of the contaminants is not critical and may be as high as 500,000. A typical molecular weight range of polymeric contaminants is 1000 to 300,000, more typically 5000 to 200,000.

The membrane used is hydrophobic and may be either a non-porous or a nano-filtration membrane. The membrane should be hydrophobic, since the stream to be treated is a hydrocarbon (-like) stream, which should be capable of passing through the membrane. The membrane suitably has a thickness of about 0.5 to about 10 μm, more suitably from about 1 to about 5 μm. The membrane is typically supported on at least one substrate layer to provide the necessary mechanical strength. Such membranes are often referred to as composite membranes or thin film composites. Generally, a composite membrane may be composed of a non-porous or nano-filtration membrane supported on a micro-filtration or ultra-filtration membrane or on another porous material. This substrate may in return be supported on a further porous support to provide the required mechanical strength. The non-porous or nano-filtration membrane may also be used without a substrate, but it will be understood that in such a case the thickness of the membrane should be sufficient to withstand the pressures applied. A thickness greater than about 10 μm may then be required. This is not preferred from a process economics viewpoint, as such thick membrane will significantly limit the throughput of the membrane, thereby decreasing the amount of purified product which can be recovered per unit of time and membrane area.

Hydrophobic nano-filtration membranes are known in the art and (potential) applications described are, for instance, the treatment of waste streams, separating dissolved lubricating oils from organic solvents, separating organic catalyst complexes from organic solvents or separating low molecular weight oligomers dissolved in organic solvents in paint wastes.

In general, nano-filtration membranes which are useful for the purpose of the present invention should have a cut-off value in terms of molecular weight of 400–5000 Dalton. Suitable hydrophobic nano-filtration composite membranes and their preparation are, for instance, disclosed in U.S. Pat. Nos. 5,205,934 and 5,265,734, both of which are hereby incorporated by reference. These composite membranes comprise an underlying porous substrate membrane, such as a micro-filtration or ultra-filtration membrane, which substrate may have been treated with a pore protector prior to coating it with a silicone layer which subsequently is crosslinked. Examples of suitable substrate materials are polyacrylonitrile, polyvinylidene fluoride, polyether imide and polyamide imide. The pore protector may be a hydroxy-terminated polysiloxane. The final silicone coating and the pore-protecting silicone layer typically have a thickness of 50–500 nm. Another example of suitable hydrophobic nano-filtration composite membranes is disclosed in U.S. Pat. No. 5,151,182, hereby incorporated by reference, and comprises a crosslinked layer having a thickness of less than about 1 $\mu$m, which layer includes a polysulfone type polymer and/or a polyphenylene oxide type polymer as well as at least one chloro- or bromomethylated polyphenylene oxide type polymer supported on a solvent stable porous membrane substrate. Crosslinking is effected by using an amine as crosslinking agent. The substrate suitably is insolubilised polyacrylonitrile.

The coated substrate membrane may be supported on a porous support to increase the mechanical strength. Examples of suitable support materials include polyethylene, polypropylene, nylon, vinyl chloride polymers, aromatic polyimides, polystyrene, polysulfon, polyesters such as polyethylene terephthalate, glass fibers, and inorganic supports based on alumina and/or silica. The composite membrane may have any desired shape, e.g. cylindrical or planar.

In case a non-porous membrane is used, transmission of the permeate takes place via the solution-diffusion mechanism: the hydrocarbons to be permeated dissolve in the membrane matrix and diffuse through the thin selective membrane layer, after which they desorb at the permeate side. The main driving force for permeation is hydrostatic pressure.

An advantage of using hydrophobic non-porous membranes as compared to the use of nano-filtration membranes is that there is no plugging effect, i.e. there is no possibility of the membrane becoming blocked by larger molecules plugged in the pores. This could happen in porous membranes, as a result of which it is more difficult to regenerate the flux. Therefore, it is preferred for the purpose of the present invention to use a non-porous membrane. However, it is emphasised that nano-filtration membranes could also be used in the process of the present invention.

Non-porous membranes as such are known in the art and in principle any hydrophobic non-porous membrane capable of retaining 80% by weight or more of compounds having a molecular weight of at least 1000 and through which hydrocarbon products as specified above can be transmitted via the solution-diffusion mechanism, can be used. Typically such membranes are crosslinked to provide the necessary network for avoiding dissolution of the membrane when in contact with a liquid hydrocarbon product. Crosslinked non-porous membranes are well known in the art. In general, crosslinking can be effected in several ways, for instance by reaction with crosslinking agents, and can optionally be enhanced by irradiation.

One example of suitable, presently available crosslinked non-porous membranes is crosslinked silicone rubber-based membranes, of which the polysiloxane membranes are a particularly useful group of membranes. Typically, the polysiloxanes contain the repeating unit —Si—O—, wherein the silicon atoms bear hydrogen or a hydrocarbon group. Preferably the repeating units are of the formula (III)

—[Si(R)(R')—O—]$_n$—                                            (III)

In the above formula, R and R' may be the same or different and represent hydrogen or a hydrocarbon group selected from the group consisting of alkyl, aralkyl, cycloalkyl, aryl, and alkaryl. Preferably, at least one of the groups R and R' is an alkyl group, and most preferably both groups are methyl groups. Very suitable polysiloxanes for the purpose of the present invention are (—OH or —NH$_2$ terminated) polydimethylsiloxanes. The cross-linking is then effected through the reactive terminal —OH or —NH$_2$ group of the polysiloxane. Preferred polysiloxane membranes are crosslinked elastomeric polysiloxane membranes. Also other rubbery non-porous membranes could be used. In general, rubbery membranes can be defined as membranes having a non-porous top layer of one polymer or a combination of polymers, of which at least one polymer has a glass transition temperature well below the operating temperature, i.e. the temperature at which the actual separation takes place. Yet another group of potentially suitable non-porous membranes are the so-called superglassy polymers. An example of such a material is polytrimethylsilylpropyne.

One example of suitable crosslinked elastomeric polysiloxane membranes are extensively described in U.S. Pat. No. 5,102,551, which is hereby incorporated by reference. Thus, suitable membranes are composed of a polysiloxane polymer such as described supra having a molecular weight of 550 to 150,000, preferably 550 to 4200 (prior to cross-linking), which is cross-linked with, as cross-linking agent, (i) a polyisocyanate, or (ii) a poly(carbonyl chloride) or (iii) $R_{4-a}Si(A)_a$ wherein A is —OH, —NH$_2$, —OR, or —OOCR, a is 2, 3, or 4, and R is hydrogen, alkyl, aryl, cycloalkyl, alkaryl, or aralkyl. Further details regarding suitable polysiloxane membranes can be found in U.S. Pat. No. 5,102,551.

For the purpose of the present invention the preferred non-porous membrane is a crosslinked polydimethylsiloxane membrane.

As indicated herein before the non-porous membrane may be used as such, but may also be supported on a substrate layer of another material. Such substrate layer could be a microporous substrate as described supra in relation to nano-filtration membranes, i.e. it could for instance be a substrate made of polyacrylonitrile, polyvinylidene fluoride, polyether imide or polyamide imide.

The non-porous membrane should preferably retain at least 80% by weight but most preferably at least 99% by weight of all compounds having a molecular weight of 1000 or more. The fraction of compounds having a molecular weight between 250 and 1000 that will be retained by the membrane will depend on the degree of crosslinking of the membrane, the stage cut, the temperature and the interaction between the fluids to be separated and the membrane. In general, the higher the degree of crosslinking and the lower the stage cut, the lower the fraction of compounds having a molecular weight between 250 and 1000 that will pass through the membrane and will end up in the permeate. The lower the degree of crosslinking and the higher the stage cut, the higher the fraction of compounds having a molecular weight between 250 and 1000 that will end up in the permeate. At higher temperatures the retention of higher molecular weight components will deteriorate. Furthermore, since a non-porous membrane does not have a sharp cut-off value, compounds having a lower molecular weight will pass more easily through the non-porous membrane than compounds having a higher molecular weight.

It is preferred that the liquid hydrocarbon product is contacted with the hydrophobic non-porous or nano-filtration membrane at a trans-membrane pressure in the range of from about 2 to about 80 bar, more preferably about 10 to about 50 bar, a flux of between about 200 and about 5000 kg/m² membrane per day (kg/m²d), more preferably about 250 to about 2500 kg/m²d, and a temperature in the range of from about 10 to about 80° C., more preferably about 10 to about 40°C.

As indicated supra, one of the advantages of the process according to the present invention is that all high molecular weight contaminants are effectively removed. This is beneficial for subsequent processing or for direct end use of the purified hydrocarbon product. It was found that in one particular case a purified hydrocarbon product resulted in a marked improvement of the properties of a subsequent product, for which it served as a reactant. Namely, when dicyclopentadiene, purified in accordance with the present invention, is used for preparing unsaturated polyester resins, a significant improvement in the product properties of the polyester resin was observed. Thus, in a further aspect, the present invention relates to the use of the purified dicyclopentadiene product obtained by the process of the present invention for the preparation of unsaturated polyester resins.

It is well known in the art that unsaturated polyester resins can be prepared by reacting an unsaturated dicarboxylic acid or its anhydride with a polyhydric alcohol and dicyclopentadiene. The resin thus formed is then recovered and blended with an ethylenically unsaturated monomer copolymerizable with the unsaturated polyester polymers to form a blend. Suitable ethylenically unsaturated monomers are well known and include: styrene, methyl styrene, chlorostyrene, vinyl toluene, divinyl benzene and the like. Examples of suitable unsaturated dicarboxylic acids or anhydrides thereof include unsaturated acids/anhydrides like maleic acid, maleic anhydride, fumaric acid, which may be used in combination with aromatic and aliphatic dicarboxylic acids. As the polyhydric alcohol diols, such as ethylene glycol, diethylene glycol, propylene glycol, and the like, may be used. The reaction between alcohol, dicarboxylic acid and dicyclopentadiene is typically carried out at a temperature of about 100° C. to about 220° C.

The invention is further illustrated by the following examples without limiting the scope of the invention to these specific embodiments.

Example 1

The experiments were performed using a hydrophobic membrane consisting of a non-porous crosslinked polydimethylsiloxane (PDMS) layer having a thickness of 2 $\mu$m supported on an ultra-filtration polyetherimide (PEI) membrane. The membrane was mounted in a flow cell having an inlet for the feed, an outlet for the permeate an outlet for the retentate. The effective membrane area was 100 cm².

The feed was fed from a storage vessel into the flow cell using a feed pump and was circulated over the membrane with a flow of 414 l/h. The permeate was recovered as product while the retentate was recycled to the storage vessel.

The feed was a stream of dicyclopentadiene (DCPD) containing 85% by weight of dicyclopentadiene, the remaining 15% by weight being formed by $C_5$ diolefin derivatives like (co)dimers, (co)trimers, (co)quadrimers etc. and polymeric substances.

Approximately 2 kg permeate was produced by passing the feed through the membrane at 30 bar and 29° C. with an average flux of 399 kg/m²d. The stage cut was 50%. To avoid oxidation upon contact with air the permeate was collected under a nitrogen atmosphere.

Both permeate and retentate were analysed using gas chromatography (GC) and GPC in combination with a refractive index detector. The GC analysis was carried out to compare the content of low molecular weight (<250) components in permeate and retentate. Polymeric substances could not be detected by the GC analysis; for these substances the GPC analysis was carried out. The GPC results are indicated in the FIGURE.

The GC data showed that all compounds having a molecular weight below 250 were not retained by the membrane. The GPC results showed that the polymeric contaminant in the retentate had a molecular weight ranging from 5000 to 200,000 with a weight average at 62,000. The polymeric contaminant was found to be polyisoprene and had a concentration of 1560 mg/l in the retentate. The polymeric contaminant was completely absent in the permeate as is clearly shown in the FIGURE.

What is claimed is:

1. A process for purifying a dicyclopentadiene product stream comprising 5% by weight or less of high molecular weight contaminants having a molecular weight of at least 5000, said process comprising:

contacting the dicyclopentadiene stream with a hydrophobic non-porous or nano-filtration membrane to produce a purified dicyclopentadiene stream; and, recovering the purified dicyclopentadiene stream as permeate.

2. A process for purifying a liquid dicyclopentadiene product stream comprising 5% by weight or less of high molecular weight contaminants having a molecular weight of at least 5000, said process comprising:

contacting the product stream with a hydrophobic non-porous or nano-filtration membrane to produce a purified product stream; and, recovering the purified product stream as permeate; and, preparing unsaturated polyester resins from the purified dicyclopentadiene product.

* * * * *